United States Patent [19]

Kettner et al.

[11] Patent Number: 4,652,552

[45] Date of Patent: Mar. 24, 1987

[54] TETRAPEPTIDE METHYL KETONE INHIBITORS OF VIRAL PROTEASES

[75] Inventors: Charles A. Kettner; Bruce D. Korant, both of Wilmington, Del.

[73] Assignee: E. I. Du Pont de Nemours and Company, Wilmington, Del.

[21] Appl. No.: 648,595

[22] Filed: Sep. 10, 1984

[51] Int. Cl.[4] ............................................ A61K 37/02
[52] U.S. Cl. ..................................................... 514/18
[58] Field of Search .................... 260/112.5 R; 514/18

[56] References Cited

U.S. PATENT DOCUMENTS 4,511,504  4/1985  McCullagh et al. ......... 260/112.5 R

OTHER PUBLICATIONS

Lozitskii et al., *Usp. Sovrem. Biol.* 93:352 (1982).
Korant, *J. Virol.* 10:751 (1972).
Summers et al., *J. Virol.* 10:880 (1972).
Korant et al., *PNAS USA* 76:2992 (1979).
Powers, "Halomethyl Ketone Inhibitors of Proteolytic Enzymes," in Weinstein, ed., *Chemistry and Biochemistry of Amino Acids, Peptides, and Proteins,* (Dekker, New York, 1977) pp. 65–178.
Powers et al., *Biochim. Biophys. Acta* 480:246 (1977).
Ito et al., *Biochem. Biophys. Res. Comm.* 49:343 (1972).
Fittkau et al., *Peptides* 1982 p. 617 (1983).
Enzyme Systems Products (product bulletin, Nov. 1981).

*Primary Examiner*—Delbert R. Phillips

[57] ABSTRACT

Certain peptide methyl ketone derivatives inhibit picornavirus replication by inhibition of virus-specified protease activity.

9 Claims, No Drawings

TETRAPEPTIDE METHYL KETONE INHIBITORS OF VIRAL PROTEASES

BACKGROUND OF THE INVENTION

The present invention relates generally to inhibitors of viral proteases, and particularly to certain peptide methyl ketones useful as specific inhibitors of protein processing by picornavirus proteases.

Proteases are enzymes which cleave proteins at specific peptide bonds. In living systems, highly specific proteases and complementary protease inhibitors mediate or control a broad spectrum of biological functions. For example, proteases cleave precursors to form active proteins in post-translational processing of polypeptides, provide mechanisms for zymogen activation cascade reactions such as blood coagulation, fibrinolysis, and complement reactions of the immune system, and mediate transport of selected proteins across biological membranes. Accordingly, proteases represent potential targets for therapeutic agents designed to function as specific inhibitors of protease activity.

Proteases encoded by viral genomes play a critical role in viral reproduction. Viral proteases cleave large precursor polypeptides produced by infected cells into smaller protein components, or subunits, which are subsequently assembled to form functional virus structures. Lozitskii et al., *Usp. Sovrem. Biol.* 93:352-362 (1982), discuss the role of proteolysis in reproduction of avian and mammalian viruses, and have surveyed part of the literature relating to viral protease inhibitors.

Picornaviruses represent a significant class of viral pathogens in humans and other mammals. Included within this class are polioviruses, rhinoviruses, and the viruses which are the etiologic agents of hepatitis A and hoof-and-mouth disease. During picornavirus replication, viral mRNA is translated in a continuous passage of ribosomes along a viral mRNA molecule, producing a linear protein product which is cleaved at selected sites by virus-specified proteases prior to dissociation of a protein/ribosome complex.

A number of workers have sought specific inhibitors of picornavirus protease activity. Korant, *J. Virol.* 10:751-759 (1972), discloses inhibition of poliovirus and echovirus-12 protein processing by chloromethyl ketone derivatives of simple amino acids. Specifically, Korant discloses inhibition by tolylsulfonylphenylalanyl chloromethyl ketone (TPCK) and tolylsulfonyllysyl chloromethyl ketone (TLCK). Summers et al., *J. Virol.* 10:880-884 (1972), similarly disclose inhibition of protease cleavage of large poliovirus-specific polypeptides by TPCK, TLCK, and D- and L-isomers of carbobenzyloxyphenylalanyl chloromethyl ketone (ZPCK). In a subsequent report, Korant et al., *Proc. Natl. Acad. Sci. USA* 76:2992-2995 (1979), describe inhibition of poliovirus protein processing by carbobenzyloxyleucyl chloromethyl ketone (ZLCK).

Various peptide derivatives with capacity to inhibit protease activity are known. Powers, "Haloketone Inhibitors of Proteolytic Enzymes", in *Chemistry and Biochemistry of Amino Acids, Peptides, and Proteins*, Weinstein, ed., (Marcel Dekker, New York, 1977), pp. 65-178, has surveyed the literature relating to inhibition of protease activity by haloketone derivatives of amino acids and peptides. Powers et al., *Biochim. Biophys. Acta* 480:246-261 (1977), disclose inhibition of subtilisin BPN', a bacterial protease, by a species of peptide chloromethyl ketones. Of the compounds tested, acetyl-L-phenylalanyl-L-glycyl-L-alanyl-L-leucyl chloromethyl ketone (Ac-Phe-Gly-Ala-LeuCH$_2$Cl) was the fastest inhibitor. A related compound, methoxysuccinyl-L-phenylalanyl-L-glycyl-L-alanyl-L-leucyl chloromethyl ketone (MeOSuc-Phe-Gly-Ala-LeuCH$_2$Cl) is disclosed by Enzyme Systems Products in a November 1981 product bulletin.

Ito et al., *Biochem. Biophys. Res. Commun.* 49:343-349 (1972), describe experiments involving inhibition of chymotrypsin, a digestive protease, by certain peptide aldehydes. Ito et al. also tested for inhibition of chymotrypsin by Ac-Leu-Leu-PheCH$_3$, a tripeptidyl methyl ketone. However, no inhibition was observed at an inhibitor concentration of 600 μg/mL.

Finally, Fittkau et al., "Synthesis and Properties of Peptide Ketones", in *Peptides 1982*, Blaha et al., eds., (de Gruyter, New York, 1983) pp. 617-622, disclose inhibition of thermitase, a thermostable serine protease of *Thermoactinomyces vulgaris*, by certain peptide methyl ketones.

It has now been found that a selected group of peptide methyl ketones are inhibitors of picornavirus protease activity. These compounds represent possible therapeutic agents for treatment of viral infection in mammals.

SUMMARY OF THE INVENTION

The present invention provides compounds of the formula

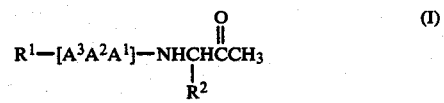

or a physiologically acceptable salt thereof, wherein
A$^1$ is an amino acid residue selected from the group consisting of Ala, Val, Leu, Ile, Phe, Tyr, Gly, Pro, Ser and Thr;
A$^2$ is an amino acid residue selected from the group consisting of Ala, Val, Leu, Ile, and Gly;
A$^3$ is an amino acid residue selected from the group consisting of Ala, Val, Leu, Ile, Phe, Tyr and Gly;
R$^1$ is an N-terminal protecting group; and
R$^2$ is methyl, isopropyl, isobutyl, 4-hydroxybenzyl, or

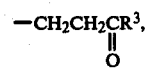

where R$^3$ is amino, methoxyl, ethoxyl, benzyloxy or alkyl of 1 to 6 carbon atoms;
provided that where A$^1$ is Ala, A$^2$ is Gly, A$^3$ is Phe and R$^2$ is isobutyl, R$^1$ cannot be Boc.

The invention also provides antiviral compositions comprising one or more of the foregoing compounds, and methods of using such compositions in treatment of picornavirus infections in mammals.

DETAILED DESCRIPTION OF THE INVENTION

The compounds of the present invention are selected tetrapeptide methyl ketones capable of inhibiting the activity of virus-specified proteases.

As used throughout the specification, the following abbreviations for amino acid residues of amino acids apply:

Ala: L-alanine
Gly: glycine
Gln: L-glutamine
Glu: L-glutamic acid
Leu: L-leucine
Ile: L-isoleucine
Lys: L-lysine
Phe: L-phenylalanine
Pro: L-proline
Ser: L-serine
Thr: L-threonine
Tyr: L-tyrosine
Val: L-valine As used throughout the specification, "N-terminal protecting group" means an arylcarbonyl, alkylcarbonyl, alkoxycarbonyl, aryloxycarbonyl, aralkoxycarbonyl, arylsulfonyl, alkylsulfonyl, or arylsulfonyl peptide protecting group, or other equivalents known to those skilled in the art of peptide synthesis. Gross and Meienhofer, eds., *The Peptides,* Vol. 3, (Academic Press, New York, 1981) pp. 3–81, the disclosure of which is hereby incorporated by reference, describe numerous suitable amine protecting groups. As used herein, either individually or as part of a larger group, "alkyl" means a linear, cyclic, or branched-chain aliphatic moiety of 1 to 10 carbon atoms; "aryl" means an aromatic moiety, e.g., phenyl, of 6 to 18 carbon atoms, unsubstituted or substituted with one or more alkyl, nitro, alkoxy, or halo groups; and "aralkoxy" means an aryl moiety of 7 to 19 carbons having an aliphatic substituent, and, optionally, other substituents such as one or more alkyl, alkoxy, nitro or halo groups. As used herein, "halo" means Cl or Br.

Examples of suitable values for N-terminal protecting group $R^1$ include formyl, acetyl, trifluoroacetyl, benzyloxycarbonyl (carbobenzoxy), substituted benzyloxycarbonyl, tert-butyloxycarbonyl, isopropyloxycarbonyl, allyloxycarbonyl, phthaloyl, benzoyl, acetoacetyl, chloroacetyl, phenoxycarbonyl, methoxysuccinyl, succinyl, 2,4-dinitrophenyl, dansyl, p-methoxybenzenesulfonyl, p-toluenesulfonyl, methanesulfonyl and phenylthio.

Certain values for N-terminal protecting group $R^1$ are abbreviated as follows throughout the specification:

Z: Carbobenzoxy
Boc: t-Butyloxycarbonyl
Ac: Acetyl
Et: Ethyl
Suc: Succinyl
MeOSuc: Methoxysuccinyl
DNS: Dansyl
DNP: 2,4-Dinitrophenyl In naming compounds of the invention, C-terminal amino acid moiety

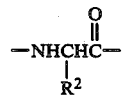

is assigned the name of a corresponding amino acid. Thus, a compound of formula I, above, wherein $R^1$ is Z, $A^1$ is Leu, $A^2$ is Gly, $A^3$ is Phe, and $R^2$ is isobutyl is conventionally named N-carbobenzoxy-L-phenylalanyl-L-glycyl-L-leucyl-L-leucyl methyl ketone; this compound is abbreviated herein as Z-Phe-Gly-Leu-LeuCH$_3$.

The scope of the present invention was defined by reference to a closely related class of compounds which were empirically determined to be inhibitors of picornavirus protease activity. These compounds, which are halomethyl ketone derivatives of selected tri- and tetrapeptides, are designated by a nomenclature system similar to that described above. In the following formula II, $A^1$, $A^2$, $A^3$, and $R^1$ are defined as set forth above for formula I. In formula II, X is Cl or Br; $R^4$ is methyl, isopropyl, isobutyl, 4-hydroxybenzyl or

where $R^5$ is amino, methoxyl, ethoxyl, benzyloxy or alkyl of 1 to 6 carbon atoms; and n is 0 or 1.

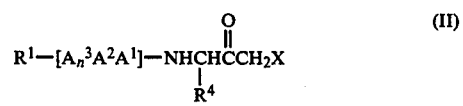

Thus, a compound of formula II, above, wherein $R^1$ is Z, $A^1$ is Leu, $A^2$ is Gly, $A^3$ is Phe, n is 1, $R^4$ is isobutyl, and X is Cl, is conventionally named N-carbobenzoxy-L-phenylalanyl-L-glycyl-L-leucyl-L-leucyl chloromethyl ketone. This compound is appreciated herein as Z-Phe-Gly-Leu-LeuCH$_2$Cl.

Preferred peptide methyl ketones of the invention are compounds of formula I wherein $R^2$ is isobutyl and $R^1$ is Z, MeOSuc, Suc, DNS or DNP. Particularly preferred compounds of the present invention are compounds of formula I wherein $R^2$ is isobutyl; $R^1$ is Z, or MeOSuc; and $A^1$, $A^2$, and $A^3$ are selected from the group consisting of Phe, Gly, Ala and Leu.

On the basis of demonstrated activity in inhibiting the growth of picornaviruses, those compounds of formula I wherein $R^2$ is isobutyl; $R^1$ is MeOSuc or Z; $A^1$ is Ala or Leu; $A^2$ is Gly; and $A^3$ is either Phe or Leu represent the most preferred class of compounds within the scope of the present invention.

Specific examples of compounds within the scope of the present invention include Z-Phe-Gly-Ala-LeuCH$_3$;
MeOSuc-Phe-Gly-Leu-LeuCH$_3$;
Z-Phe-Gly-Leu-LeuCH$_3$;
Ac-Phe-Gly-Ala-LeuCH$_3$;
Suc-Phe-Gly-Ala-LeuCH$_3$;
MeOSuc-Phe-Gly-Ala-LeuCH$_3$;
DNS-Phe-Gly-Ala-LeuCH$_3$;
DNP-Phe-Gly-Ala-LeuCH$_3$;
Z-Leu-Gly-Ala-LeuCH$_3$;
Z-Phe-Gly-Gly-LeuCH$_3$;
Z-Phe-Leu-Ala-LeuCH$_3$;
Z-Phe-Gly-Phe-LeuCH$_3$;
Z-Phe-Gly-Ser-LeuCH$_3$;
Z-Phe-Gly-Pro-LeuCH$_3$;
MeOSuc-Ala-Ile-Phe-LeuCH$_3$;
Z-Phe-Gly-Ala-ValCH$_3$;
Z-Phe-Gly-Ala-TyrCH$_3$;
MeOSuc-Phe-Gly-Leu-Glu(OMe)CH$_3$ and
MeOSuc-Ala-Ile-Phe-Glu(OMe)CH$_3$.

Physiologically acceptable salts of compounds of formula I include acid addition salts of free base, if present, wherein the acid can be organic or inorganic, e.g., hydrochloric, phosphoric, maleic, acetic, citric, succinic, etc. Alternatively, salts of free peptidic acids, including sodium, potassium, and ammonium salts, are included within the scope of the present invention.

In practicing the antiviral processes of the invention, the foregoing compounds can be employed alone, in combination with one another, in combination with other therapeutic agents, or in combination with various inert pharmaceutically acceptable carriers in a variety of dosage forms, orally or parenterally. Dose requirements will vary with the compound and dosage form employed and the animal being treated. Typically, therapy is initiated at lower dosages and dosage is increased until the desired inhibiting effect is achieved.

The compounds of the instant invention can be prepared by techniques generally corresponding to those disclosed by Kettner et al., *Arch. Biochem. Biophys.* 162:56 (1974), and Kettner et al., *Arch. Biochem. Biophys.* 165:739 (1974).

First, N-protected peptides or amino acids are reacted with about one equivalent of N-methylmorpholine and one equivalent of isobutyl chloroformate at about −20° C., generating a mixed peptide-isobutyric acid anhydride. This standard techniqud is described by Anderson, et al., *J. Amer. Chem. Soc.* 89:5012 (1967). Second, the resulting mixed anhydride is treated with about one equivalent of diazomethane in tetrahydrofuran or other suitable inert, aprotic solvent at 0° C., generating an N-protected peptide or amino acid diazomethyl ketone. Third, the latter compound is treated with a solution of HCl or HBr in anhydrous ethanol or ether at 0° C., producing an N-protected halomethyl ketone. Fourth, methyl ketones can be generated from the corresponding N-protected halomethyl ketones by hydrogenolysis in anhydrous methanol, employing 10% palladium on charcoal as catalyst.

Larger peptide halomethyl ketones can be assembled by repetitively coupling a deprotected halomethyl ketone to mixed anhydrides of other N-protected peptides or amino acids generated according to the foregoing procedure. Deprotection of N-terminal amino groups can be accomplished by treatment with trifluoroacetic acid, anhydrous HF, anhydrous HCl, or by other methods known to those skilled in the art.

Corresponding peptide methyl ketones can be prepared by analogous coupling procedures in which a deprotected methyl ketone rather than a halomethyl ketone is employed. Specific examples of these procedures are disclosed in Examples 1 and 2 below.

Generally applicable procedures suitable for producing compounds within the scope of the present invention are described in the paragraphs preceding the Examples, below. In the synthetic procedures and Examples, all parts and percentages are by weight, and all degrees are Celsius, unless otherwise noted.

GENERAL SYNTHETIC PROCEDURES

1. Mixed Anhydride Coupling Procedure (MA)

Approximately 1-2 g of an N-protected amino acid or peptide are dissolved in 20 mL of tetrahydrofuran (THF), and the resulting solution is cooled to −20°. N-methylmorpholine (1 eq) and isobutyl chloroformate (1 eq) are added and after 5 minutes, an additional 10 mL of cold THF and one equivalent of triethylamine are added. The resulting mixture is immediately added to an equivalent of an amine hydrochloride or trifluoroacetate dissolved in 5 mL of dimethylformamide (DMF). The ensuing reaction is allowed to stir 1 hour at −20° and then 2 hours at about 23°. The resulting mixture is filtered and the filtrate thereby obtained is then concentrated to approximately 5 mL by evaporation. The resulting concentrate or residue is dissolved in ethyl acetate, and then washed sequentially with 0.2N hydrochloric acid, 5% sodium bicarbonate solution, and saturated aqueous sodium chloride. The resulting organic solution is then dried briefly over sodium sulfate, filtered, and finally evaporated to leave a crude peptide product.

2. N-Hydroxysuccinimide (OSu) Coupling Procedure

N-hydroxysuccinimide esters of N-protected amino acids and peptides can be prepared by procedures substantially similar to those described by Anderson et al., *J. Am. Chem. Soc.* 86:1839 (1964). An OSu ester is dissolved in a minimal volume of dioxane, and the resulting solution is added to an equal volume of an aqueous solution consisting of 1.5 eq of triethylamine and either an amino acid (1.5 eq) or a peptide (1.1 eq), forming a reaction mixture. After about 5 minutes, if a complete solution is not obtained, a small test sample of the reaction mixture can be diluted with water and another sample diluted with dioxane. On the basis of the results obtained, the reaction mixture is then diluted with the appropriate solvent (either water or dioxane) until completely dissolved. After the reaction has proceeded to completion, the reaction mixture is acidified with hydrochloric acid and the resulting product extracted into ethyl acetate. The resulting extract is then washed with 0.2N hydrochloric acid followed by 0.2N hydrochloric acid in saturated sodium chloride. The washed extract is then dried over sodium sulfate, filtered, and finally evaporated to dryness to leave a crude peptide.

3. Other Coupling Procedures

Dansyl, 2,4-dinitrophenyl, and methoxysuccinyl derivatives of peptides are prepared by reacting a selected chloride, fluoride, or N-hydroxysuccinimide ester with an appropriate peptide. Acetyl and succinyl derivatives can be prepared from corresponding anhydrides. A peptide hydrochloride or trifluoroacetate salt is dissolved in 50% aqueous dioxane at a level of 0.25 mmol/mL and the resulting solution is cooled to 0°. A selected coupling agent (1.0–1.2 eq) is dissolved in dioxane and added along with 2 eq of sodium bicarbonate. The resulting reaction is monitored by following the disappearance of ninhydrin positive material.

4. Saponification of Methyl Esters

An N-protected methyl ester is dissolved in dioxane (1 mL/mmole), and an equal volume of 1.00N sodium hydroxide is added over a period of 30 minutes. Disappearance of starting material is monitored by thin-layer chromatography. After the resulting reaction has proceeded to completion, an equivalent of 1.00N hydrochloric acid is added, and the solution is diluted to 100 mL with water. The product is then extracted into ethyl acetate, and the resulting extract washed with 0.2N hydrochloric acid followed by 0.2N hydrochloric acid in saturated sodium chloride. Solvent is then removed by evaporation to leave a crude carboxylic acid.

5. Hydrolysis of the Boc Group

Boc protecting groups are removed from peptides by dissolving a selected peptide in trifluoroacetic acid and stirring the resulting solution for 5 minutes at about 23°.

Cold ether is then added. If a precipitate is obtained upon addition of ether, it is triturated with ether and isolated. If no precipitate is obtained, the ether is evaporated and toluene added to co-evaporate residual trifluoroacetic acid, yielding the deprotected peptide as a trifluoroacetic acid salt.

Alternatively, a Boc-protected peptide can be dissolved in ethanolic hydrochloric acid (2.0–3.5N) and the resulting solution stirred at about 23° for about 30 minutes, followed by evaporation of solvent. In all cases, peptide hydrochloride or trifluoroacetate salts are dried overnight under vacuum in the presence of solid potassium hydroxide and phosphorus pentoxide.

6. Hydrolysis of t-butyl Esters (Bu)

t-Butyl peptide esters are dissolved in trifluoroacetic acid, and the resulting solution is stirred for 1 hour at about 23° C. Solvent is then evaporated, and the resulting residue is redissolved in toluene. Following a second toluene evaporation step, the remaining residue is dried in vacuo over solid potassium hydroxide. Crude product is crystallized from an appropriate solvent, e.g., toluene or ethyl acetate.

7. Thin-Layer Chromatography (TLC) Procedures

TLCs are run on 5×10 cm silica gel plates, using a fluorescent indicator. Spots are visualized by conventional techniques, using either UV light or an iodine jar. Peptides with free amino groups protected by Boc groups are exposed to HCl vapors, and then stained with ninhydrin. The following solvent systems are useful for chromatograpy:
methanol:chloroform (1:9)
butanol:acetic acid:water (4:1:1)
ethyl acetate:hexane (8:2)

EXAMPLE 1

Synthesis of Z-Phe-Gly-Ala-LeuCH$_3$

H-LeuCH$_3$.HBr was prepared by a procedure substantially similar to that disclosed by Kettner et al., *Arch. Biochem. Biophys.* 165:739 (1974). Z-Phe-Gly-Ala-OH was prepared according to the following procedure. An N-hydroxysuccinimide ester of Z-Phe-OH was dissolved in dioxane, and the resulting solution filtered into a solution containing about one equivalent of H-Gly-Ala-OH, about 1.5 equivalents triethylamine, and water. The resulting reaction mixture was stirred overnight at about 23°, and then concentrated to approximately 60% of its original volume by evaporation. This concentrated solution was then diluted with 1.0N hydrochloric acid until acidic. The resulting product was extracted into ethyl acetate, and the resulting extract washed with 0.2N hydrochloric acid followed by saturated aqueous sodium chloride adjusted to 0.1N hydrochloric acid. The washed extract was then dried over anhydrous sodium sulfate and filtered. Solvent was then evaporated from the extract to provide product Z-Phe-Gly-Ala-OH as a foam. This crude product was recrystallized from ethyl acetate.

Z-Phe-Gly-Ala-OH was coupled to H-LeuCH$_3$.HBr as follows. First, a mixed anhydride of Z-Phe-Gly-Ala-OH was prepared by dissolving Z-Phe-Gly-Ala-OH (1.22 g, 2.85 mmol) and N-methylmorpholine (0.32 mL, 2.85 mmol) in 35 mL tetrahydrofuran. The resulting solution was cooled to about −20°, and 0.25 mL (1.90 mmol) isobutyl chloroformate was added. After 10 minutes, the resulting solution was added to H-LeuCH$_3$.HBr (0.40 g, 1.90 mmol) dissolved in 5 mL cold dimethylformamide containing 0.26 mL (1.90 mmol) triethylamine. The resulting mixture was stirred for 1 hour at −20°, allowed to warm to about 23°, and then stirred overnight at about 23°. The resulting solution was filtered, and then evaporated to a volume of about 5 mL. 100 mL ethyl acetate was added and the resulting solution was washed sequentially with 5% sodium bicarbonate, 0.2N hydrochloric acid, and saturated aqueous sodium chloride. After drying over sodium sulfate and filtering to remove undissolved material, solvent was removed by evaporation to yield 0.88 g of a white solid, which was recrystallized from hot ethyl acetate to provide a first crop (0.27 g. m.p. 133°–134°) and a second crop (0.25 g, m.p. 133.5°–134°). Thin layer chromatography in MeOH:CHCl$_3$ (1:9, V:V) indicated a single spot, Rf 0.48. NMR spectra were consistent with predicted structure:

Anal: Calcd. for C$_{29}$H$_{38}$N$_4$O$_6$: C, 64.65; H, 7.12; N, 10.40. Found: C, 64.51; H, 6.91; N, 10.56.

EXAMPLE 2

Preparation of MeOSuc-Phe-Gly-Leu-LeuCH$_3$

Z-Phe-Gly-Leu-LeuCH$_3$ was prepared by coupling Z-Phe-Gly-Leu-OH (2.23 g, 4.76 mmol) to H-LeuCH$_3$.HBr by a procedure substantially similar to that described for preparation of Z-Phe-Gly-Ala-LeuCH$_3$ in Example 1, above. Product was recrystallized from ethyl acetate to yield 2.34 g of Z-Phe-Gly-Leu-LeuCH$_3$ (m.p. 165.5°–166.5°).

Anal. Calcd. for C$_{32}$H$_{44}$N$_4$O$_6$: C, 66.26; H, 7.66; N, 9.66. Found: C, 66.48; H, 7.75; N, 9.66.

Z-Phe-Gly-Leu-LeuCH$_3$ (1.0 g, 1.72 mmol) was dissolved in 100 mL of absolute ethanol to which 0.5 g of 10% palladium on carbon and 0.5 mL of 4N ethanolic HCl were added. The resulting mixture was hydrogenated at an initial pressure of 40 psi (276 kPa) overnight. Catalyst was removed by filtration, and then solvent was evaporated to yield a foam, 0.85 g, which solidified after addition of ether. This product was extensively washed with ether and dried in vacuo over solid potassium hydroxide and phosphorus pentoxide.

H-Phe-Gly-Leu-LeuCH$_3$.HCl (0.62 g, 1.29 mmol) and the N-hydroxysuccinimide ester of methyl succinate (0.30 g, 1.29 mmol) were dissolved in 5 mL of N,N-dimethylformamide, and then triethylamine (0.18 mL, 1.29 mmol) was added. After stirring overnight, 5 mL of 5% aqueous sodium bicarbonate were added, and the resulting solution was stirred for 15 minutes. The resulting product was extracted into ethyl acetate. The extract was washed sequentially with 5% aqueous sodium bicarbonate, 0.2N hydrochloric acid, and saturated aqueous sodium chloride. The washed extract was dried over anhydrous sodium sulfate and filtered. Solvent was then evaporated to yield product as an oil. Product crystallized from ethyl acetate:hexane to yield 0.68 g of MeOSuc-Phe-Gly-Leu-LeuCH$_3$ (m.p. 113.5°–114°).

Anal: Calcd. for C$_{29}$H$_{41}$N$_4$O$_7$: C, 62.45; H, 7.42; N, 10.05. Found: C, 62.09; H, 7.82; N, 10.10.

Biological Activity of Selected Tetrapeptide Methyl Ketones

Selected compounds of the present invention have been shown to inhibit viral protease activity in two assays. One assay, designated the viral cleavage assay, involves comparison of patterns of protein synthesis (as visualized by incorporation of labeled amino acids) in virus-infected HeLa cells grown in the presence and absence of a selected test compound. A second assay, known as a plaque inhibition assay, involves an assessment of the effects of test compounds upon the infectivity of virus in agar-overlaid cell cultures. Toxic effects of a test compound, if any, will also be observed during the incubation period of the plaque inhibition assay, Both assays are described in greater detail below.

Viral Cleavage Assay

In this assay, samples of growing HeLa-O cells were exposed to human poliomyelitis virus type 2 or human rhinovirus type 1A at a virus concentration of about 10 infectious virus particles per cell. After several hours, host cell metabolism was markedly inhibited, and added radioactive amino acids were incorporated into viral proteins only. After varying concentrations of a test compound were added to cell samples, viral proteins were labeled for 60 minutes at the approximate mid-cycle of infection (3–5 hours after first exposure of the cells to the virus). Cell samples were then solubilized in 0.01M tris(hydroxymethyl)aminomethane buffer, pH 6.8, containing 1% (w/v) sodium dodecyl sulfate and 1% (v/v) 2-mercaptoethanol. The resulting radiolabeled viral proteins were separated by polyacrylamide gel electrophoresis, and then detected by autoradiography, as previously described by Korant et al., *Proc. Natl. Acad. Sci. USA* 76:2992 (1979). If a selected concentration of a test compound disrupted the usual pattern of virus protein processing, that compound was scored as active at the concentration tested. Gels corresponding to cell samples labeled in the presence of test compounds exhibiting viral protease-inhibiting activity were generally distinguishable by appearance of high molecular weight protein species not apparent on control gels.

Plaque Inhibition Assay

In this assay, cultured HeLa cells were grown to confluency in 60 mm plastic petri dishes. Each culture was then infected with approximately 300 plaque-forming units of virus. Poliovirus type 2 and rhinovirus type 1A were used in the tests reported below. The virus employed in a given experiment was allowed to absorb to the cells for 30 minutes at 34.5°.

Each compound to be tested was dissolved in ethanol or dimethylsulfoxide at a concentration 100 times greater than the highest concentration to be tested. The resulting solution was then diluted 1:100 into a solution of McCoy's medium containing 5% heat-inactivated fetal calf serum and 0.38% agar. Two-fold dilutions were then made into agar medium.

After virus adsorbed to the cells, excess virus was washed away and each culture dish was overlaid with 5 mL of agar medium containing a pre-selected dilution of the compound to be tested. Control cultures were overlaid with agar medium only. Each culture was then incubated at 34.5° for two to five days, depending upon the virus used, to allow development of plaques.

A plaque is a roughly circular region of dead cells in a culture, indicating an area where one plaque-forming unit of virus first infected one cell. The agar overlay restricts virus mobility, so that viral infection was communicated only between contiguous cells.

When plaques in control cultures were large enough to be easily observed, yet still relatively discrete, all cultures were stained with 1% crystal violet. Plaques appeared as clear areas in a deep purple field of uninfected cells. Toxic doses of a test compound resulted in visible cell detachment in culture dishes.

EXAMPLES 3–5

Assay of Tetrapeptide Methyl Ketones for Viral Protease-Inhibiting Activity in Viral Cleavage Assay The following compounds demonstrated activity in the viral cleavage assay against poliovirus type 2 and rhinovirus type 1A at a test concentration of 100 µg/mL. The compounds Z-Phe-Gly-Ala-LeuCH$_3$ and MeOSuc-Phe-Gly-Leu-LeuCH$_3$ were also active at 50 µg/mL against poliovirus type 2. The compound Boc-Phe-Gly-Ala-LeuCH$_3$ failed to show activity in this assay.

| Example | Compound |
|---------|----------|
| 3 | Z—Phe—Gly—Ala—LeuCH$_3$ |
| 4 | MeOSuc—Phe—Gly—Ala—LeuCH$_3$ |
| 5 | Z—Phe—Gly—Leu—LeuCH$_3$ |

EXAMPLE 6

Assay of Z-Phe-Gly-Ala-LeuCH$_3$ for Antiviral Activity in Plaque Inhibition Assay The compound Z-Phe-Gly-Ala-LeuCH$_3$ provided plaque reduction in excess of 90% with both poliovirus type 2 and rhinovirus type 1A, compared to control plates, when incorporated into agar overlays at a concentration of 50 µg/mL. No cytotoxicity was observed in assays involving this compound at concentrations up to 1 mg/mL.

COMPARATIVE EXPERIMENTS 1–30

Protease-Inhibiting Activity of Corresponding Tetrapeptide Chloromethyl Ketones in Viral Cleavage Assay As noted previously, the scope of compounds representing the present invention was established by prediction based upon observed antiviral activity of analogous chloromethyl ketone derivatives. The results of a series of viral cleavage assays in which protease-inhibiting activities of representative tetrapeptide and tripeptide chloromethyl ketones were evaluated are set forth in Table 1, below. The results are reported as follows:

| | |
|---|---|
| no activity | − |
| low activity | +/− |
| active at 100 µg/mL | + |
| active at 50 µg/mL | ++ |
| active at 10 µg/mL | +++ |
| active at <5 µg/mL | ++++ |

TABLE 1

Protease-Inhibiting Activity of Selected Peptide Chloromethyl Ketones

| Peptide Analog | Activity |
|----------------|----------|
| 1. Z—Phe—Gly—Ala—LeuCH$_2$Cl | +++ |
| 2. H—Phe—Gly—Ala—LeuCH$_2$Cl | +/− |
| 3. Ac—Phe—Gly—Ala—LeuCH$_2$Cl | +++ |
| 4. Suc—Phe—Gly—Ala—LeuCH$_2$Cl | +++ |
| 5. MeOSuc—Phe—Gly—Ala—LeuCH$_2$Cl | +++ |
| 6. DNS—Phe—Gly—Ala—LeuCH$_2$Cl | +++ |
| 7. DNP—Phe—Gly—Ala—LeuCH$_2$Cl | +++ |
| 8. Boc—Gly—Ala—LeuCH$_2$Cl | ++ |
| 9. Z—Ala—Gly—Ala—LeuCH$_2$Cl | +/− |
| 10. Z—Leu—Gly—Ala—LeuCH$_2$Cl | +++ |

TABLE 1-continued

Protease-Inhibiting Activity of Selected Peptide Chloromethyl Ketones

| Peptide Analog | Activity |
| --- | --- |
| 11. Z—Gln—Gly—Ala—LeuCH$_2$Cl | + |
| 12. Z—Phe—Gly—Gly—LeuCH$_2$Cl | +++ |
| 13. Z—Phe—Gly—Ala—LeuCH$_2$Br | +++ |
| 14. Z—Phe—Gly—Ala—ValCH$_2$Cl | ++ |
| 15. Z—Phe—Gly—Leu—LeuCH$_2$Cl | ++++ |
| 16. Z—Phe—Leu—Ala—LeuCH$_2$Cl | ++ |
| 17. Z—Phe—Gly—Phe—LeuCH$_2$Cl | ++ |
| 18. Z—Phe—Phe—Ala—LeuCH$_2$Cl | +/− |
| 19. Z—Phe—Gly—Ser—LeuCH$_2$Cl | ++ |
| 20. Z—Phe—Ser—Ala—LeuCH$_2$Cl | + |
| 21. Z—Phe—Gly—Lys—LeuCH$_2$Cl | + |
| 22. Z—Phe—Lys—Ala LeuCH$_2$Cl | + |
| 23. Z—Phe—Gly—Pro—LeuCH$_2$Cl | ++ |
| 24. Z—Phe—Pro—Ala—LeuCH$_2$Cl | + |
| 25. Ac—Phe—Gly—Glu—LeuCH$_2$Cl | +/− |
| 26. Ac—Phe—Glu(OEt)—Ala—LeuCH$_2$Cl | +/− |
| 27. MeOSuc—Ala—Ile—Phe—LeuCH$_2$Cl | +++ |
| 28. MeOSuc—Phe—Gly—Leu—Glu(OCH$_3$)CH$_2$Cl | ++++ |
| 29. MeOSuc—Ala—Ile—Phe—Glu(OCH$_3$)CH$_2$Cl | +++ |
| 30. Ac—Phe—Glu—Ala—LeuCH$_2$Cl | +/− |

What is claimed is:

1. A method of treating a picornavirus infection in a mammal, comprising administering to the mammal an effective antiviral amount of a compound of the formula

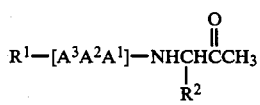

or a physiologically acceptable salt thereof, wherein
$A^1$ is an amino acid residue selected from the group consisting of Ala, Val, Leu, Ile, Phe, Tyr, Gly, Pro, Ser and Thr;
$A^2$ is an amino acid residue selected from the group consisting of Ala, Val, Leu, Ile, and Gly;
$A^3$ is an amino acid residue selected from the group consisting of Ala, Val, Leu, Ile, Phe, Tyr and Gly;
$R^1$ is an N-terminal protecting group; and
$R^2$ is methyl, isopropyl, isobutyl, 4-hydroxybenzyl, or

where $R^3$ is amino, methoxyl, ethoxyl, benzyloxy, or alkyl of 1-6 carbon atoms;
provided that where $A^1$ is Ala, $A^2$ is Gly, $A^3$ is Phe and $R^2$ is isobutyl, $R^1$ cannot be Boc.

2. A method according to claim 1 wherein
$A^1$ is selected from the group consisting of Ala, Val, Leu, Ile, Phe, Gly, Pro, and Ser;
$A^2$ is selected from the group consisting of Ala, Val, Leu, Gly and Ile;
$A^3$ is selected from the group consisting of Ala, Val, Leu, Ile, and Phe;
$R^1$ is Z, Ac, Boc, MeOSuC, Suc, DNS or DNP; and
$R^2$ is isopropyl or isobutyl.

3. A method according to claim 2 wherein
$A^1$ is Ala, Val, Leu, Gly, Pro or Ser;
$A^2$ is Ala, Val, Leu or Gly;
$A^3$ is Ala, Val, Leu, or Phe;
$R^1$ is Z, MeOSuc or Suc; and
$R^2$ is isopropyl or isobutyl.

4. A method according to claim 3 wherein
$A^1$ is Ala, Val, Leu or Gly;
$A^2$ is Leu or Gly;
$A^3$ is Phe or Leu;
$R^1$ is Z or MeOSuc; and
$R^2$ is isopropyl or isobutyl.

5. A method according to claim 4 wherein
$A^1$ is Ala or Leu;
$A^2$ is Gly;
$A^3$ is Phe;
$R^1$ is Z or MeOSuc; and
$R^2$ is isobutyl.

6. A method according to claim 5 wherein
$A^1$ is Ala; and
$R^1$ is Z.

7. A method according to claim 5 wherein
$A^1$ is Leu; and
$R^1$ is Z.

8. A method according to claim 4 wherein
$A^1$ is Gly;
$A^2$ is Gly;
$A^3$ is Phe;
$R^1$ is Z; and
$R^2$ is isobutyl.

9. A method according to claim 4 wherein
$A^1$ is Ala;
$A^2$ is Leu;
$A^3$ is Phe;
$R^1$ is Z; and
$R^2$ is isobutyl.

* * * * *